(12) United States Patent
Takeshita et al.

(10) Patent No.: US 10,226,202 B2
(45) Date of Patent: Mar. 12, 2019

(54) CONTACT-ANGLE MEASUREMENT METHOD, CONTACT-ANGLE MEASUREMENT DEVICE, BIOPROSTHETIC-MEMBER INSPECTION DEVICE, AND STORAGE MEDIUM

(71) Applicant: KYOCERA Medical Corporation, Osaka-shi, Osaka (JP)

(72) Inventors: Yohei Takeshita, Osaka (JP); Akio Muranaka, Osaka (JP); Kiyotaka Utsumi, Osaka (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 245 days.

(21) Appl. No.: 14/907,941

(22) PCT Filed: Oct. 15, 2014

(86) PCT No.: PCT/JP2014/077439
§ 371 (c)(1),
(2) Date: Jan. 27, 2016

(87) PCT Pub. No.: WO2015/064363
PCT Pub. Date: May 7, 2015

(65) Prior Publication Data
US 2016/0166179 A1 Jun. 16, 2016

(30) Foreign Application Priority Data

Oct. 30, 2013 (JP) ................................. 2013-225538

(51) Int. Cl.
*G06T 7/20* (2017.01)
*A61B 5/107* (2006.01)
(Continued)

(52) U.S. Cl.
CPC .......... *A61B 5/1071* (2013.01); *G01B 11/255* (2013.01); *G01B 11/26* (2013.01);
(Continued)

(58) Field of Classification Search
None
See application file for complete search history.

(56) References Cited

U.S. PATENT DOCUMENTS 5,137,352 A     8/1992   Blitshteyn et al.
5,428,990 A *   7/1995   Ohmi ....................... G01N 1/40
                                                                     73/53.06
(Continued)

FOREIGN PATENT DOCUMENTS

CN         102654442 A     9/2012
EP          0694778 A1     1/1996
(Continued)

OTHER PUBLICATIONS

International Search Report, PCT/JP2014/077439, dated Dec. 9, 2014, 2 pgs.
(Continued)

*Primary Examiner* — Nancy Bitar
(74) *Attorney, Agent, or Firm* — Volpe and Koenig, P.C.

(57) ABSTRACT

This contact-angle measurement method is a contact-angle measurement method for measuring a contact angle (γ) between a droplet that is supplied to a sample curved surface and the sample curved surface. This method includes an apparent contact-angle calculation step of calculating an apparent contact-angle (α) of the droplet by using a captured image of the droplet supplied to the sample curved surface and the sample curved surface; an inclination angle calculation step of calculating an inclination angle (β) of the sample curved surface at an outer periphery portion of a contact portion between the droplet and the sample curved (Continued)

surface by using the captured image; and a contact-angle calculation step of calculating the contact angle ($\gamma$) by correcting the apparent contact angle ($\alpha$), using the inclination angle ($\beta$).

19 Claims, 7 Drawing Sheets

(51) Int. Cl.
*G01N 13/02* (2006.01)
*G01B 11/255* (2006.01)
*G01B 11/26* (2006.01)
*A61F 2/46* (2006.01)

(52) U.S. Cl.
CPC ............... *G01N 13/02* (2013.01); *G06T 7/20* (2013.01); *A61F 2/468* (2013.01); *G01N 2013/0208* (2013.01)

(56) References Cited

U.S. PATENT DOCUMENTS

| | | | |
|---|---|---|---|
| 7,952,698 B2 | 5/2011 | Friedrich et al. | |
| 9,103,969 B2 | 8/2015 | Biteau et al. | |
| 9,612,167 B2* | 4/2017 | Dyshlyuk | G01N 25/4853 |
| 2009/0180106 A1* | 7/2009 | Friedrich | G01N 13/02 |
| | | | 356/138 |
| 2012/0164458 A1* | 6/2012 | Biteau | G02B 1/105 |
| | | | 428/447 |
| 2012/0197407 A1 | 8/2012 | Kyomoto et al. | |

FOREIGN PATENT DOCUMENTS

| | | |
|---|---|---|
| JP | 2012-529663 A | 11/2012 |
| JP | 5265388 B2 | 8/2013 |
| WO | 2010/142798 A1 | 12/2010 |
| WO | 2011/021642 A1 | 2/2011 |

OTHER PUBLICATIONS

Extended European Search Report, European Patent Application No. 14858757.9, dated Jun. 9, 2017, 7 pgs.
Chinese Office Action with English Translation and English concise explanation, Chinese Patent Application No. 201480043521.3, dated Jun. 2, 2017, 14 pgs.
Viswanadam, G., et al., "Contact angles of drops on curved superhydrophobic surfaces," Journal of Colloid and Interface Science, 367 (2012), pp. 472-477.
Guilizzoni, M., "Drop shape visualization and contact angle measurement on curved surfaces," Journal of Colloid and Interface Science, 364 (2011), pp. 230-236.

* cited by examiner

CONTACT-ANGLE MEASUREMENT METHOD, CONTACT-ANGLE MEASUREMENT DEVICE, BIOPROSTHETIC-MEMBER INSPECTION DEVICE, AND STORAGE MEDIUM

TECHNICAL FIELD

The present invention relates to a contact-angle measurement method, a contact-angle measurement device, a bioprosthetic-member inspection device, and a storage medium.

BACKGROUND ART

A contact-angle measurement method for measuring the contact angle of a given droplet on a sample surface is known (see Patent Document 1, for example). The contact-angle measurement method disclosed in Patent Document 1 is a method for obtaining a contact angle ($\varphi$) from a sample surface (3), a gaseous environment, and a droplet (5) that is located on the sample surface (3) and that includes a curved surface (7), the axis of symmetry (ASy-ASy), and a predetermined volume (VI). This contact-angle measurement method includes steps (a) to (d). In step (a), an image of a subject is formed based on the reflection properties of the surface (7) of the droplet (5), the position of the subject relative to the optical axis (A-A) of the optical measurement system and the position of the subject relative to the sample surface (3), which are both known, and the axis of symmetry (ASy-ASy) of the droplet (5) that is located on or in the vicinity of the optical axis (A-A). In step (b), the distance between the image of the subject and the axis of symmetry (ASy-ASy) of the droplet (5) is obtained. In step (c), the radius of the curved surface of the droplet (5) is obtained by using the measured distance. In step (d), the contact angle ($\varphi$) is obtained by using the radius of the curved surface.

CITATION LIST

Patent Document

Patent Document 1: Japanese Patent No. 5265388 (Claim 1)

DISCLOSURE OF THE INVENTION

Problem to be Solved by the Invention

In some cases, the contact-angle measurement method is used for measuring the hydrophilic properties (the wettability) of the surface of an artificial hip joint member or the like. An artificial hip joint includes a bone head ball and a liner in which a dent has been formed, and the bone head ball is fitted into the liner. The bone head ball and the liner are thus brought into sliding-contact. In this configuration, in some cases, a coating layer is formed on the liner, in order to improve the abrasion resistance. In such cases, it is preferable to inspect the wettability of the coating layer when manufacturing the liner, in order to examine whether or not the coating layer of the liner can provide the desired performance. The contact-angle measurement method is used for this wettability inspection. That is, the contact angle between a droplet provided on the surface of the coating layer and the coating layer is measured, and the wettability is determined based on this contact angle.

The dent surface in the liner has the shape of a curved surface, and according to the contact-angle measurement method, the contact angle of the droplet provided on the curved surface is measured. However, according to Patent Document 1, as can be seen from FIG. 2 and the equations shown in Appendix 1, cases where the sample surface is a curved surface are not taken into consideration. In other words, with the configuration disclosed in Patent Document 1, correction is not performed when the sample surface is a curved surface, and therefore there is the concern that the contact angle cannot be precisely measured when the sample surface is a curved surface.

In light of the aforementioned circumstances, an object of the present invention is to provide a contact-angle measurement method, a contact-angle measurement device, a bioprosthetic-member inspection device, and a storage medium with which the contact angle on a sample curved surface can be more precisely measured.

Means for Solving the Problem (1) A contact-angle measurement method for achieving the above-described object according to one aspect of the present invention is a contact-angle measurement method for measuring a contact angle $\gamma$ (the true contact angle) between a droplet that is supplied to a sample curved surface and the sample curved surface, including; an apparent contact-angle calculation step of calculating an apparent contact-angle $\alpha$ of the droplet by using a captured image of the droplet supplied to the sample curved surface and the sample curved surface; an inclination angle calculation step of calculating an inclination angle $\beta$ of the sample curved surface at an outer periphery portion of a contact portion between the droplet and the sample curved surface by using the captured image; and a contact-angle calculation step of calculating the contact angle $\gamma$ by correcting the apparent contact angle $\alpha$, using the inclination angle $\beta$.

With this configuration, the apparent contact angle is corrected by using the inclination angle of the sample curved surface. In other words, the true contact angle that takes the shape of the sample curved surface into consideration is calculated. Consequently, the contact-angle measurement method makes it possible to more precisely measure the contact angle of the sample curved surface.

(2) Preferably, the apparent contact angle $\alpha$ is an angle formed by: a plane that includes a tangent line to an outer surface of the droplet at a given point on the outer periphery portion, and that is in contact with the outer surface; and a plane that includes the outer periphery portion.

With such a configuration, an angle with reference to the outer periphery portion of the droplet is set as the apparent contact angle.

(3) Preferably, the inclination angle $\beta$ is an angle formed by: a plane that includes a tangent line to the sample curved surface at a given point on the outer periphery portion, and that is in contact with the sample curved surface; and a plane that includes the outer periphery portion.

With such a configuration, an angle with reference to the outer periphery portion of the droplet is set as the inclination angle.

(4) Preferably, a step of calculating a curvature radius Ra of the outer surface of the droplet by using a curvature radius C of the outer periphery portion, a volume V0 of the droplet, and a curvature radius Rb of the sample curved surface, is included as a step that precedes the apparent contact-angle calculation step, and in the apparent contact-angle calculation step, the apparent contact angle α is calculated by using the curvature radius Ra and the curvature radius C.

With this configuration, it is relatively difficult to measure the curvature radius Ra of the outer surface of the droplet supplied to the sample curved surface that is not flat, directly from the captured image. In contrast, it is relatively easy to measure the curvature radius C of the outer periphery portion of the droplet from the captured image, for example. Also, it is relatively easy to measure the volume V0 of the droplet by measuring the droplet ejected from the nozzle. Also, it is relatively easy to obtain the curvature radius Rb of the sample curved surface from the design data of the sample or the like. Therefore, it is easy to calculate the curvature radius Ra of the outer surface of the droplet by using the curvature radius C of the outer periphery portion, the volume V0 of the droplet, and the curvature radius Rb of the sample curved surface, as data that can be relatively easily obtained. It is then possible to calculate the apparent contact angle α by applying the curvature radius Ra of the outer surface and the curvature radius C of the outer periphery portion to the trigonometric functions, for example.

(5) Preferably, the curvature radius Ra of the outer surface is calculated by using the following Formulas (a), (b), and (c):

$$Va = (4\pi/3)Ra^3 - (\pi/3)\{(Ra^2-C^2)^{(1/2)}+Ra\}^2\{3Ra-(Ra^2-C^2)^{(1/2)}-Ra\}; \quad (a)$$

$$Vb = (4\pi/3)Rb^3 - (\pi/3)\{(Rb^2-C^2)^{(1/2)}+Rb\}^2\{3Rb-(Rb^2-C^2)^{(1/2)}-Rb\}; \text{ and} \quad (b)$$

$$V0 = Va+Vb \text{ (when the sample curved surface is concave) or } V0 = Va-Vb \text{ (when the sample curved surface is convex)}, \quad (c)$$

where Va denotes a volume of a first region that is surrounded by: a plane that includes the outer periphery portion; and the outer surface of the droplet, and Vb denotes a volume of a second region that is surrounded by: the plane that includes the outer periphery portion; and the sample curved surface.

With this configuration, it is possible to calculate the volume Va of the first region by using Formula (a) for calculating the volume of a portion of a sphere. Also, it is possible to calculate the volume Vb of the second region by using Formula (b) for calculating the volume of a portion of a sphere. It is then possible to calculate the curvature radius Ra by using Formula (c) that expresses the relationship among the volume V0 of the droplet, the volume Va of the first region, and the volume Vb of the second region.

(6) Preferably, in the inclination angle calculation step, the inclination angle β is calculated by using a curvature radius C of the outer periphery portion and a curvature radius Rb of the sample curved surface.

With this configuration, it is relatively easy to measure the curvature radius C of the outer periphery portion of the droplet from the captured image, for example. Also, it is relatively easy to obtain the curvature radius Rb of the sample curved surface from the design data of the sample or the like. Therefore, it is easy to calculate the inclination angle.

(7) It is further preferable that the curvature radius C of the outer periphery portion is calculated by using the captured image.

With this configuration, the outer periphery portion can be easily seen from the outside of the droplet. Therefore, it is easy to calculate the curvature radius of the outer periphery portion based on the captured image.

(8) Preferably, the sample curved surface is a concave curved surface having a predetermined curvature radius Rb, and in the contact-angle calculation step, a value of the apparent contact angle α to which the inclination angle β has been added is calculated as the contact angle γ.

With this configuration, it is possible to calculate the true contact angle of the sample curved surface having a concave shape. The droplet on the sample curved surface having a concave shape is surrounded by the sample, and it is difficult to visually measure the contact angle from the side of the sample. However, even in such a case, it is possible to precisely calculate the true contact angle of the sample curved surface.

(9) Preferably, the sample curved surface is a convex curved surface having a predetermined curvature radius Rb, and in the contact-angle calculation step, a value of the apparent contact angle α from which the inclination angle β has been subtracted is calculated as the contact angle γ.

With this configuration, it is possible to calculate the true contact angle of the sample curved surface having a convex shape.

(10) Preferably, a volume V0 of the droplet is set to 0.5μ liters to 3.0μ liters.

With this configuration, by setting the volume of the droplet to be larger than or equal to 0.5μ liters, it is possible to reduce the amount of liquid that remains in the nozzle when the droplet is dripped from the nozzle, for example. Consequently, it is possible to sufficiently reduce the proportion of liquid that remains in the nozzle to the volume of the droplet supplied from the nozzle. Therefore, it is possible to sufficiently reduce the influence of the liquid remaining in the nozzle with respect to the droplet on the sample curved surface, and it is possible to more precisely calculate the contact angle by using the droplet. Also, by setting the volume of the droplet to be smaller than or equal to 3.0μ liters, it is possible to prevent the volume of the droplet that has dropped to the sample curved surface from becoming too large. Therefore, it is possible to reduce the influence of gravity on the droplet on the sample curved surface. Consequently, it is possible to treat the outer surface of the droplet as a portion of a virtually true sphere, and more precisely calculate the contact angle by using the droplet.

(11) A contact-angle measurement device for achieving the above-described object according to one aspect of the present invention is a contact-angle measurement device for measuring a contact angle γ between a droplet that is supplied to a sample curved surface and the sample curved surface, including; an apparent contact-angle calculation unit configured to calculate an apparent contact-angle α of the droplet by using a captured image of the droplet supplied to the sample curved surface and the sample curved surface; an inclination angle calculation unit configured to calculate an inclination angle β of the sample curved surface at an outer periphery portion of a contact portion of the droplet and the sample curved surface by using the captured image; and a contact-angle calculation unit configured to calculate the contact angle γ by correcting the apparent contact angle α, using the inclination angle β.

With this configuration, the apparent contact angle is corrected by using the inclination angle of the sample curved surface. In other words, the true contact angle that takes the shape of the sample curved surface into consideration is calculated. Consequently, the contact-angle measurement device makes it possible to more precisely measure the contact angle of the sample curved surface.

(12) A bioprosthetic-member inspection device for achieving the above-described object according to one aspect of the present invention is a bioprosthetic-member inspection device including: the above-described contact-angle measurement device; and an inspection unit configured to inspect wettability of a curved surface of a bioprosthetic member that serves as the sample curved surface, by using the contact angle γ measured by the contact angle measurement device.

With this configuration, the apparent contact angle is corrected by using the inclination angle of the sample curved surface. In other words, the true contact angle that takes the shape of the sample curved surface into consideration is calculated. Consequently, the bioprosthetic-member inspection device can more precisely measure the contact angle of the sample curved surface.

(13) A storage medium for achieving the above-described object according to one aspect of the present invention is a computer-readable storage medium that stores therein a program, the program being for measuring a contact angle γ between a droplet that is supplied to a sample curved surface and the sample curved surface, the program causing a computer to perform: an apparent contact-angle calculation step of calculating an apparent contact-angle α of the droplet by using a captured image of the droplet supplied to the sample curved surface and the sample curved surface; an inclination angle calculation step of calculating an inclination angle β of the sample curved surface at an outer periphery portion of a contact portion between the droplet and the sample curved surface by using the captured image; and a contact-angle calculation step of calculating the contact angle γ by correcting the apparent contact angle α, using the inclination angle β.

With this configuration, the apparent contact angle is corrected by using the inclination angle of the sample curved surface. In other words, the true contact angle that takes the shape of the sample curved surface into consideration is calculated. Consequently, it is possible to more precisely measure the contact angle of the sample curved surface.

Effects of the Invention

With the present invention, it is possible to more precisely measure the contact angle of the sample curved surface.

DESCRIPTION OF EMBODIMENTS

Hereinafter, modes for carrying out the present invention will be described with reference to the drawings. Note that the present invention is broadly applicable as a contact-angle measurement method, a contact-angle measurement device, a bioprosthetic-member inspection device, and a storage medium.

Figure 1:
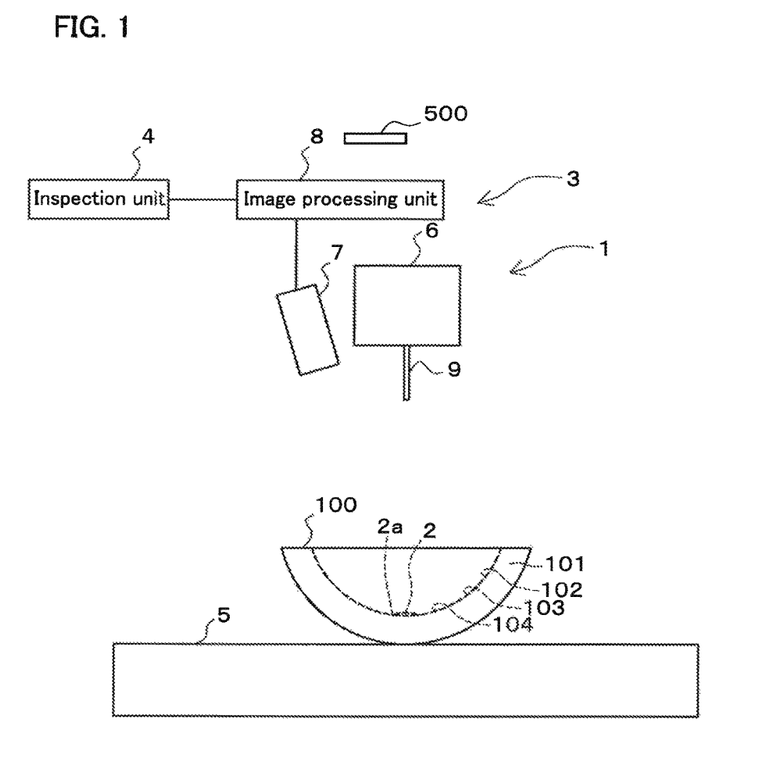
FIG. 1 is a schematic side view of a bioprosthetic-member inspection device and a sample according to an embodiment of the present invention.
Figure 2:
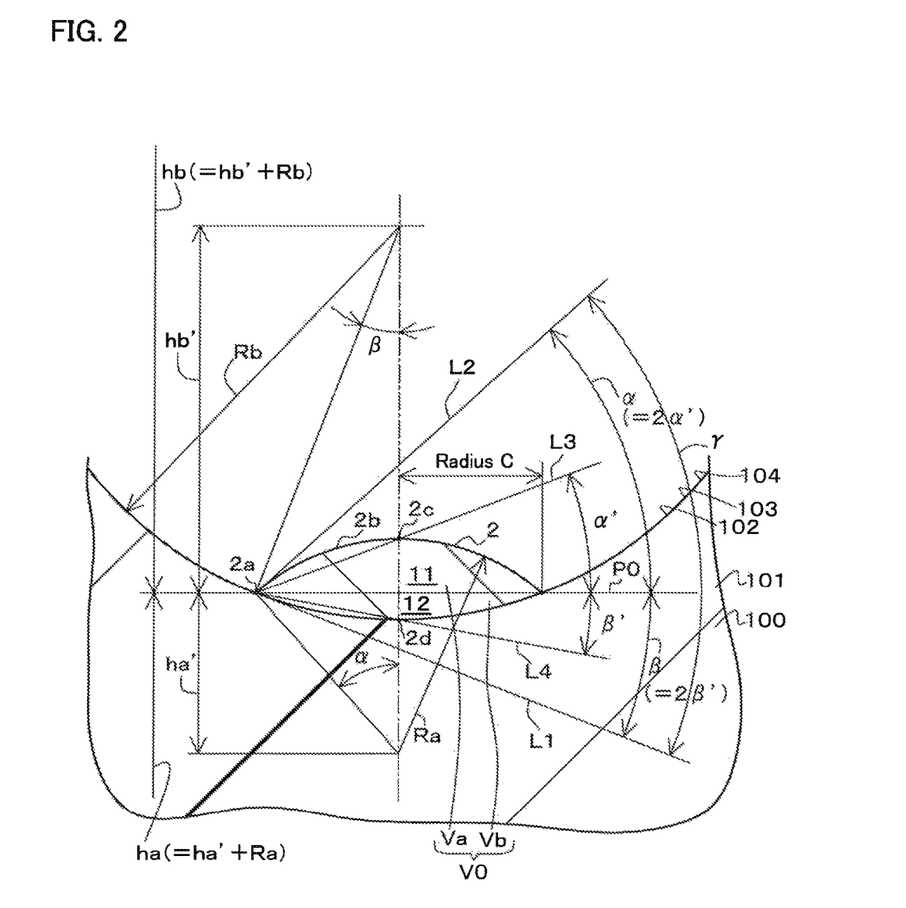
FIG. 2 is a cross-sectional view in which the sample and a droplet are enlarged.

FIG. 1 is a schematic side view of a bioprosthetic-member inspection device 1 and a sample 100 according to an embodiment of the present invention. FIG. 2 is a cross-sectional view in which the sample 100 and a droplet 2 are enlarged.

Referring to FIG. 1 and FIG. 2, the bioprosthetic-member inspection device 1 is configured to inspect the sample 100 that is made of a bioprosthetic member.

The bioprosthetic-member inspection device 1 includes a contact-angle measurement device 3 and an inspection unit 4.

The contact-angle measurement device 3 is configured to measure a contact angle γ of the droplet 2 relative to the sample 100.

The sample 100 is, for example, a liner that serves as a bioprosthetic member that is used in an artificial hip joint. The sample 100 is a member with a dent that is to be installed to an acetabulum of the patient. The sample 100 is configured so as to be brought into sliding-contact with a bone head ball at the tip of a stem that is fixed to the femur of the patient. The sample 100 is a liner that is actually installed inside the patient's body, and the contact angle γ is measured by the contact-angle measurement device 3 for every liner to be installed to the patient as the sample 100. In the present embodiment, the contact-angle measurement device 3 measures the contact angle γ of the sample 100 without using a substance that has a negative influence on the patient's health.

In the present embodiment, the sample 100 is a member formed to have a cup-like shape and has a substantially semi-spherical shape with a dent. The diameter of the sample 100 is set to approximately 35 mm to 65 mm, for example.

The sample 100 includes a base member 101 and a polymer layer 102. Examples of the material of the base member 101 include at least one of synthetic resin, metal material, and ceramic material. Examples of synthetic resin include ultrahigh molecular weight polyethylene (hereinafter also referred to as UHMWPE). Among polymer materials, UHMWPE has excellent mechanical properties such as abrasion resistance and deformation resistance, and is suited to being the base member 101. Cross-linked polyethylene that has undergone cross-linking treatment with UHMWPE may be used as the base member 101.

As described above, the base member 101 is formed to have a cup-like shape, and a dent 103 is formed. The dent 103 is formed to have a concave curved shape, and is formed to have a semi-spherical shape in the present embodiment. The polymer layer 102 is formed on the inner surface of the dent 103.

The polymer layer 102 is provided as a thin film (a coating layer), and formed integrally with the base member 101. The thickness of the polymer layer 102 is approximately several nanometers to several hundred micrometers. The polymer layer 102 is formed spanning the entire inner surface of the dent 103. The surface of the polymer layer 102 has the shape of a curved surface, and is formed to have a semi-spherical shape in the present embodiment. The surface of the polymer layer 102 constitutes a sample curved surface 104. The sample curved surface 104 is formed to have a concave semi-spherical shape with a predetermined curvature radius Rb. This curvature radius Rb is a value that is determined when the sample 100 is designed. That is, the sample curved surface 104 is a concave curved surface having the predetermined curvature radius Rb. In the present embodiment, the polymer layer 102 is formed by, for example, irradiating a monomer solution having a phosphorylcholine group with ultraviolet light, with the solution being in contact with the dent 103.

Next, a description is given of a specific configuration of the contact-angle measurement device 3.

As described above, the contact-angle measurement device 3 is configured to measure the contact angle γ between the droplet 2 supplied to the sample curved surface 104 and the sample curved surface 104. The droplet 2 is transparent water, for example. Note that the droplet 2 on the sample curved surface 104 suffices if it can be visually discerned from the sample curved surface 104, and may be a liquid other than transparent water.

The contact angle γ is the angle formed by a plane L1 related to the sample curved surface 104 and a plane L2 related to the droplet 2 (the angle on the side facing inward of the droplet 2). The contact angle γ is determined in relation with an outer periphery portion 2a of the droplet 2. The outer periphery portion 2a is the outer periphery portion of the droplet 2 when the sample 100 and the droplet 2 are viewed from above, and is a line and a circle in the present embodiment. The outer periphery portion 2a is the outer periphery portion of the droplet 2 at the contact portion of the droplet 2 and the sample curved surface 104.

The plane L1 is a plane that includes a tangent line to the sample curved surface 104 at a given point on the outer periphery portion 2a, and that is in contact with the sample curved surface 104. The plane L1 includes a plurality of tangent lines to the sample curved surface 104 at a given point on the outer periphery portion 2a. The plane L2 is a plane that includes a tangent line to an outer surface 2b of the droplet 2 at a given point on the outer periphery portion 2a, and that is in contact with the outer surface 2b. The plane L2 includes a plurality of tangent lines to the outer surface 2b at a given point on the outer periphery portion 2a.

The contact-angle measurement device 3 captures an image of the sample 100 and the droplet 2, and calculates the contact angle γ by using the captured image obtained by image capturing.

The contact-angle measurement device 3 includes a seating 5, a dripping unit 6, an image capturing unit 7, and an image processing unit 8.

The seating 5 is a stage on which the sample 100 is to be placed. The dripping unit 6 is located above the seating 5.

Figure 3:
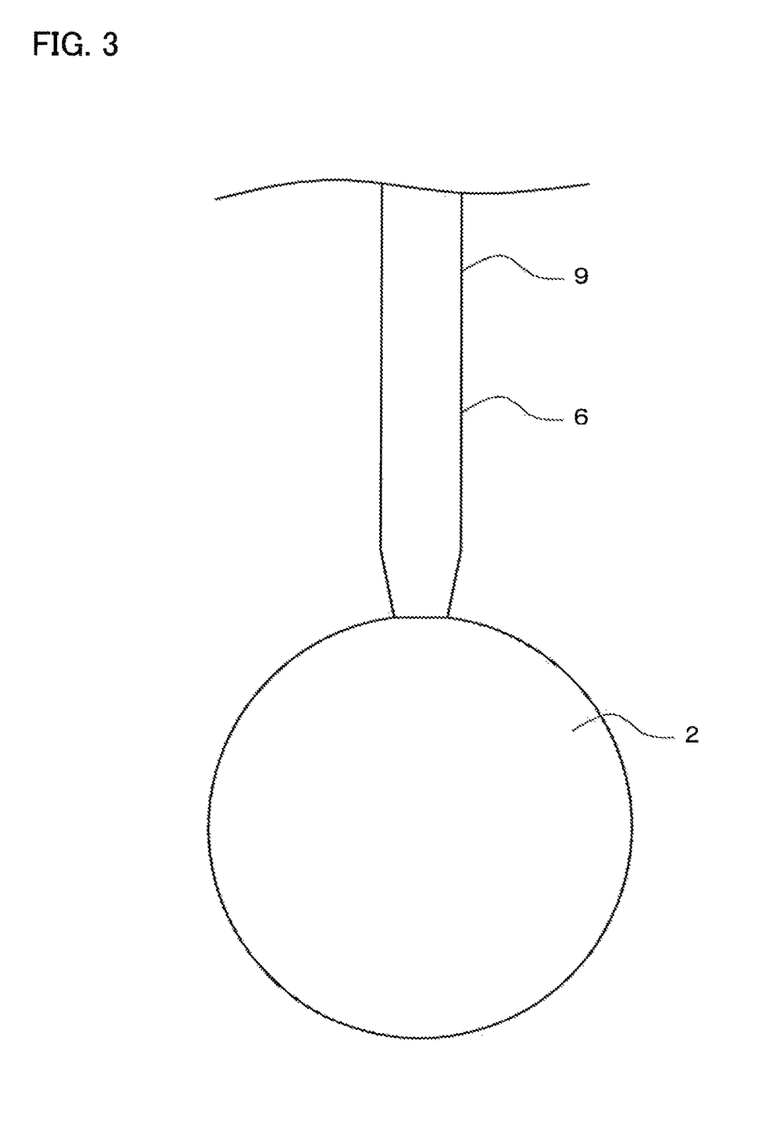
FIG. 3 is a side view in which a dripping unit is enlarged.

FIG. 3 is a side view in which the dripping unit 6 is enlarged. Referring to FIG. 1 to FIG. 3, the dripping unit 6 is provided in order to supply the droplet 2 to the sample curved surface 104. The dripping unit 6 includes a nozzle 9, and the droplet 2 having a predetermined volume V0 is dropped from the nozzle 9 onto the sample curved surface 104. The dripping unit 6 is configured to be able to precisely set the volume of the droplet 2 that drops from the nozzle 9. In the present embodiment, the volume V0 of the droplet 2 that is dripped from the dripping unit 6 and attaches to the sample curved surface 104 is set to fall within the range of 0.5μ liters to 3.0μ liters.

If the volume V0 of the droplet 2 is smaller than 0.5μ liters, the proportion of volume of the droplet 2 that remains in the nozzle 9 is large when the droplet 2 drops from the nozzle 9. Therefore, an error between the volume V0 of the droplet 2 set for the dripping unit 6 and the volume V0 of the droplet 2 that actually attaches to the sample curved surface 104 is large.

On the other hand, if the volume V0 of the droplet 2 is larger than 3.0μ liters, the volume V0 of the droplet 2 that drops onto the sample curved surface 104 is too large. Therefore, the influence of gravity on the droplet 2 on the sample curved surface 104 is large. As a result, the shape of the outer surface 2b of the droplet 2 on the sample curved surface 104 deviates from the shape that can be considered to have a single curvature radius, and a large measurement error occurs when a curvature radius C of the droplet 2, which is described below, is measured. Note that the upper limit of the volume V0 of the droplet 2 is preferably 2.0μ liters.

Referring to FIG. 1 and FIG. 2, an image of the droplet 2 that has dropped from the dripping unit 6 onto the sample curved surface 104 and the sample curved surface 104 is captured by the image capturing unit 7. The image capturing unit 7 is provided in order to capture an image of the droplet 2 and the sample curved surface 104 from above the sample 100. The image capturing unit 7 is a CCD (Charge Coupled Device) camera, for example. The image capturing unit 7 is located adjacent to the dripping unit 6, and is configured to be able to capture an image of the droplet 2 immediately before it drops from the nozzle 9.

A lens of the image capturing unit 7 is located above the droplet 2, and faces toward a top point 2c of the droplet 2. A flat image obtained by the image capturing unit 7 includes the droplet 2 having a round shape and the sample curved surface 104 having a flat shape. The image capturing unit 7 outputs image data of the captured image obtained by capturing an image of the droplet 2 and the sample curved surface 104 to the image processing unit 8.

The image processing unit 8 is configured to calculate the contact angle γ based on, for example, the image data obtained by capturing an image of the droplet 2 and the sample curved surface 104. The image processing unit 8 is an example of "an apparent contact-angle calculation unit", and an example of "an inclination angle calculation unit", and an example of "a contact-angle calculation unit" according to the present invention. The image processing unit 8 is a computer that includes, for example, a CPU (Central Processing Unit), a RAM (Random Access Memory), and a ROM (Read Only Memory).

Next, a description is given of, for example, principles (calculation formulas) for calculating the contact angle γ by the image processing unit 8.

For the calculation of the contact angle γ, first, volumes Va and Vb related to the droplet 2 and the sample 100 are calculated. The volume Va is the volume of a first region 11 that is the region surrounded by a plane P0 (a horizontal plane in the present embodiment) that includes the outer periphery portion 2a, and the outer surface 2b of the droplet 2 (the surface of an exposed portion of the droplet 2 above the sample curved surface 104). The volume Vb is the volume of a second region 12 that is the region surrounded by the plane P0 and the sample curved surface 104.

Figure 4:
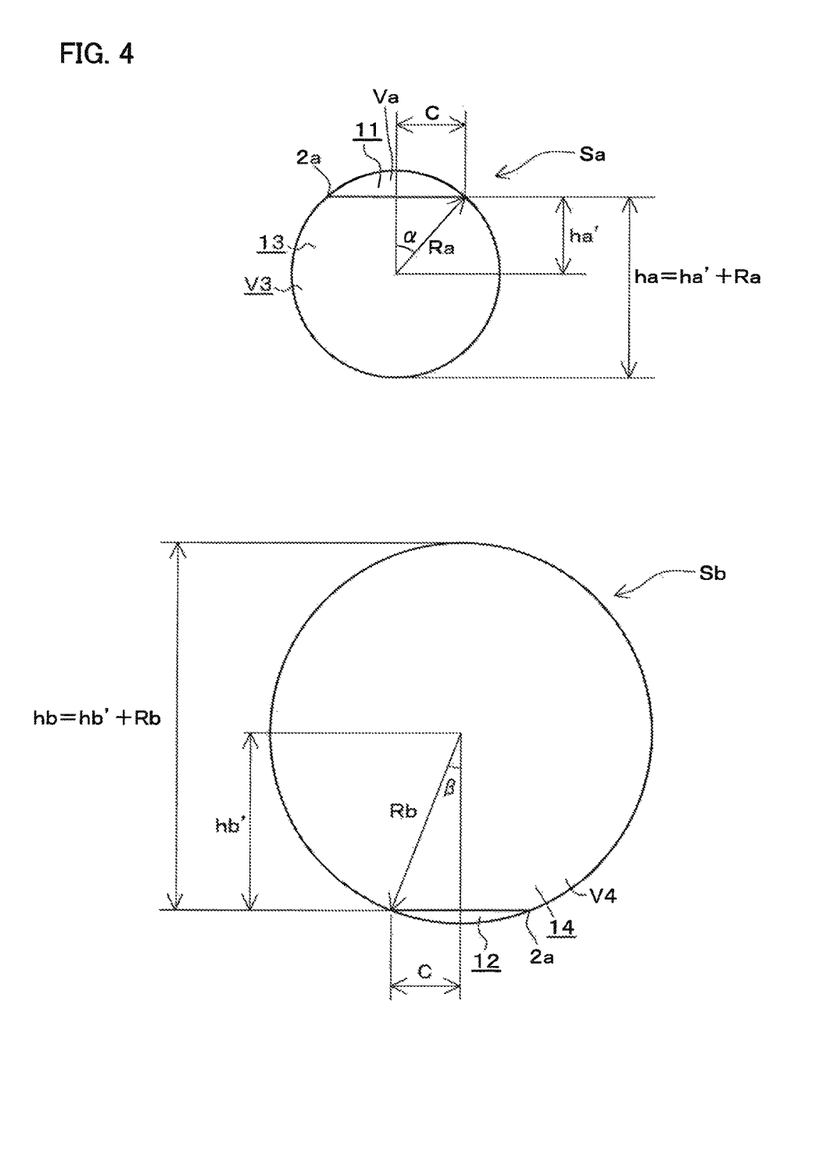
FIG. 4 is a schematic diagram illustrating volumes Va and Vb.

FIG. 4 is a schematic diagram illustrating the volumes Va and Vb. Referring to FIG. 2 and FIG. 4, the volume Va of the first region 11 is the volume of the first region 11 that is a portion of a sphere Sa that has a curvature radius Ra. Here, when ha' denotes the distance from the center point of the sphere Sa to the first region 11, the distance ha'<the curvature radius Ra is satisfied.

Here, when ha=ha'+Ra is satisfied, a volume V3 of a third region 13 of the sphere Sa other than the first region 11 is expressed by Formula (1) below obtained by performing integration on a portion of the sphere Sa:

$$V3 = \pi ha \times (3C^2 + ha^2)/6 \quad (1)$$

where C is the curvature radius of the outer periphery portion 2a of the droplet 2. The curvature radius C is expressed by Formula (2) below:

$$C = \{ha(2Ra-ha)\}^{(1/2)} \quad (2)$$

Formulas (1) and (2) above lead to:

$$V3 = \pi ha^2 \times (3Ra-ha)/3 \quad (3)$$

Therefore, the volume Va of the first region 11 is the value of the volume of the sphere Sa from which the volume V3 of the third region 13 has been subtracted. Thus:

$$Va = (4\pi/3)Ra^3 - (\pi/3)ha^2 \times (3Ra-ha) \quad (4)$$

The volume Vb of the second region 12 is the volume of the second region 12 that is a portion of the sphere Sb having the curvature radius Rb. Here, when hb' denotes the distance from the center point of the sphere Sb to the second region 12, the distance hb'<the curvature radius Rb is satisfied.

Here, when hb=hb'+Rb is satisfied, the volume Vb of the second region 12 is the value of the volume of the sphere Sb from which a volume V4 of a fourth region 14 has been subtracted, in the same manner as described above. That is, the volume Vb of the second region 12 is expressed by the formula below:

$$Vb = (4\pi/3)Rb^3 - (\pi/3)hb^2 \times (3Rb-hb) \quad (5)$$

According to the Pythagorean theorem, the relationship expressed by the formula below is satisfied:

$$Ra^2 = C^2 + ha'^2 \quad (6)$$

Therefore, $ha' = (Ra^2 - C^2)^{(1/2)}$ (7)

Also, $ha = ha' + Ra$ (8)

As with Formulas (6) to (8) above, $$Rb^2 = C^2 + hb'^2 \quad (9)$$

Therefore, $hb' = (Ra^2 - C^2)^{(1/2)}$ (10)

Also, $hb = hb' + Rb$ (11)

The above leads to Formulas (12) and (13) below:

$$Va = (4\pi/3)Ra^3 - (\pi/3)\{(Ra^2-C^2)^{(1/2)} + Ra\}^2 \{3Ra - (Ra^2-C^2)^{(1/2)} - Ra\} \quad (12)$$

$$Vb = (4\pi/3)Rb^3 - (\pi/3)\{(Rb^2-C^2)^{(1/2)} + Rb\}^2 \{3Rb - (Rb^2-C^2)^{(1/2)} - Rb\} \quad (13)$$

The first region 11 and the second region 12 are formed with the droplet 2. That is, the sum of the volume Va of the first region 11 and the volume Vb of the second region 12 is the volume V0 of the droplet 2, which is expressed by V0=Va+Vb . . . (14).

Note that Formulas (12), (13), and (14) are respectively examples of "formulas (a), (b) and (c)" according to the present invention.

Referring to FIG. 1 and FIG. 2, the image processing unit 8 can measure the curvature radius C of the outer periphery portion 2a from the captured image (the flat image) obtained by the image capturing unit 7. The image processing unit 8 can obtain the curvature radius Rb of the sample curved surface 104 from, for example, the design data of the sample 100. The image processing unit 8 can also measure (calculate) the volume V0 of the droplet 2 from the data of the captured image of the droplet 2 immediately before it drops from the nozzle 9. That is, using the curvature radius C, the curvature radius Rb, and the volume V0 of the droplet 2 as known values, the image processing unit 8 can calculate the curvature radius Ra of the first region 11 by using Formulas (12) to (14).

The angle formed by the plane L2 related to the droplet 2 and the plane P0 that includes the outer periphery portion 2a (the angle that faces toward the top point 2c of the droplet 2) is the contact angle with respect to the first region 11, and this angle is defined as an apparent contact angle α of the droplet 2.

The angle formed by the plane L1 related to the sample curved surface 104, and the plane P0, is the contact angle with respect to the second region 12, and this angle is defined as an inclination angle β of the sample curved surface 104.

As can be seen from FIG. 4, the relationships expressed by the formulas below are satisfied with the apparent contact angle α and the inclination angle β:

$$\sin(\alpha) = C/Ra \quad (15)$$

$$\sin(\beta) = C/Rb \quad (16)$$

That is, the relationships expressed by the formulas below are satisfied:

$$\alpha = \arcsin(C/Ra) \quad (17)$$

$$\beta = \arcsin(C/Rb) \quad (18)$$

Therefore, the contact angle γ is expressed by the formula below:

$$\gamma = \alpha + \beta = \arcsin(C/Ra) + \arcsin(C/Rb) \quad (19)$$

Figure 5:
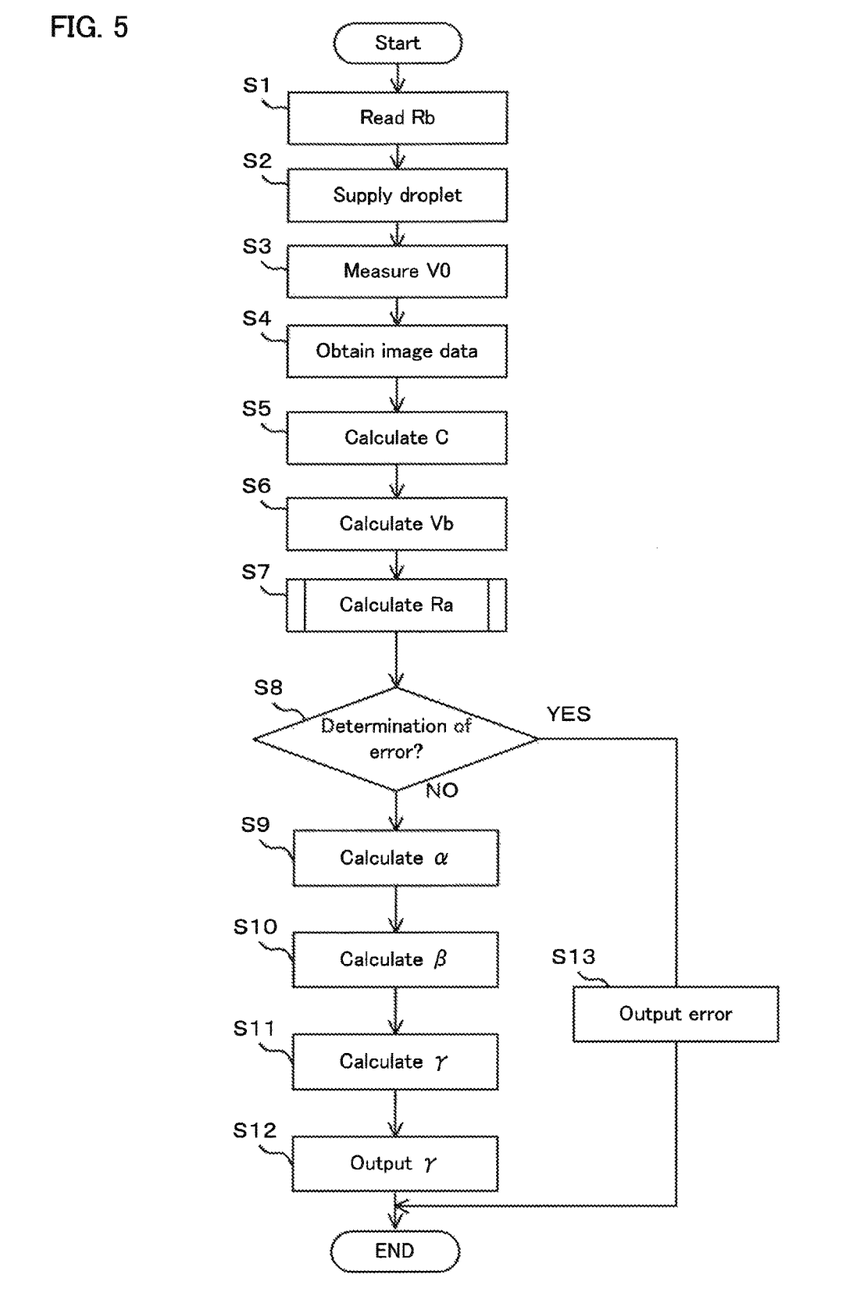
FIG. 5 is a flowchart illustrating an example of a processing flow of a contact-angle measurement device.

FIG. 5 is a flowchart illustrating an example of a processing flow of the contact-angle measurement device 3. Note that when describing the processing flow of the contact-angle measurement device 3, drawings other than FIG. 5 are also referred to as needed.

The contact-angle measurement device 3 reads out and executes the steps of the flowchart described below from a memory that is not shown in the drawings. This program can be externally installed. The program to be installed is distributed in the state of being stored in a storage medium 500 (see FIG. 1), for example. Examples of the storage medium 500 include a DVD (Digital Versatile Disc) and a CD-ROM.

The image processing unit 8 of the contact-angle measurement device 3 first reads the value of the curvature radius Rb of the sample curved surface 104 (step S1). Specifically, for example, the operator of the contact-angle measurement device 3 operates an operation unit of the contact-angle measurement device 3, which is not shown in the drawings, and thus the value of the curvature radius Rb is provided to the image processing unit 8.

Next, the dripping unit 6 supplies the droplet 2 having the predetermined volume V0 to the sample curved surface 104 (step S2). Next, the image processing unit 8 calculates the volume V0 of the droplet 2 supplied from the dripping unit 6 by using the captured image of the nozzle 9 (step S3). In this case, the image processing unit 8 calculates the volume V0 of the droplet 2 by performing integration or the like as needed on the droplet 2 from the tip of the nozzle 9 in the captured image of the nozzle 9.

Next, the image capturing unit 7 captures an image of the droplet 2 on the sample curved surface 104, and of the sample curved surface 104, and provides the data obtained by this image capturing to the image processing unit 8 (step S4).

Using the image data thus provided, the image processing unit 8 calculates the curvature radius C (the curvature radius of the outer periphery portion 2a in plan view) of the droplet 2 on the sample curved surface 104 (step S5). Consequently, the image processing unit 8 obtains the curvature radius Rb of the sample curved surface 104 and the curvature radius C of the droplet 2. Then, the image processing unit 8 calculates the volume Vb of the second region 12 based on Formula (13) (step S6).

Next, the image processing unit 8 calculates the curvature radius Ra of the outer surface 2b of the droplet 2 by using the curvature radius Rb of the sample curved surface 104, the volume V0 of the droplet 2, the curvature radius C of the droplet 2, and the volume Vb of the second region 12, as data obtained in the steps above (step S7).

The step of calculating the curvature radius Ra (step S7) is a step that is performed prior to the step of calculating the apparent contact angle $\alpha$ (step S9). In this step S7, the curvature radius Ra is calculated by using the curvature radius C of the outer periphery portion 2a, the volume V0 of the droplet 2, and the curvature radius Rb of the sample curved surface 104. The details of processing in step S7 are described below.

Next, the image processing unit 8 determines whether or not the determination of an error was made in the calculation of the curvature radius Ra in step S7 (step S8). If the determination of an error was not made (NO in step S8), the image processing unit 8 calculates the apparent contact angle $\alpha$ (step S9). Specifically, the image processing unit 8 calculates the apparent contact angle $\alpha$ by substituting the curvature radius Ra of the outer surface 2b of the droplet 2 and the curvature radius C of the outer periphery portion 2a of the droplet 2, which are obtained in the above steps, into Formula (17). That is, the image processing unit 8 calculates the apparent contact angle $\alpha$ by using the captured image of the droplet 2 supplied to the sample curved surface 104, and of the sample curved surface 104. This step S9 is an example of "an apparent contact-angle calculation step" according to the present invention.

Next, the image processing unit 8 calculates the inclination angle $\beta$ (step S10). Specifically, the image processing unit 8 calculates the inclination angle $\beta$ by substituting the curvature radius Rb of the sample curved surface 104 and the curvature radius C of the outer periphery portion 2a of the droplet 2, which are obtained in the above steps, into Formula (18). That is, the image processing unit 8 calculates the inclination angle $\beta$ of the sample curved surface 104 at the outer periphery portion 2a by using the above-described captured image. This step S10 is an example of "an inclination angle calculation step" according to the present invention.

Next, the image processing unit 8 calculates the contact angle $\gamma$ by using Formula (19) (step S11). Specifically, the image processing unit 8 calculates the contact angle $\gamma$ ($=\alpha+\beta$) by adding the inclination angle $\beta$ to the apparent contact angle $\alpha$ obtained in the above steps. That is, the image processing unit 8 corrects the apparent contact angle $\alpha$ by using the inclination angle $\beta$. This step S11 is an example of "a contact-angle calculation step" according to the present invention.

Next, the image processing unit 8 outputs data that specifies the contact angle $\gamma$ to a display unit of the contact-angle measurement device 3, which is not shown in the drawings (step S12). Consequently, the above-described display unit displays the contact angle $\gamma$.

On the other hand, if the determination of an error was made in step S8 (YES in step S8), data indicating that the determination of an error was made is output to the display unit (step S13). Consequently, the display unit displays the fact that a measurement error has occurred.

Next, a description is given of an example of the calculation of the curvature radius Ra of the outer surface 2b of the droplet 2 (step S7).

Figure 6:
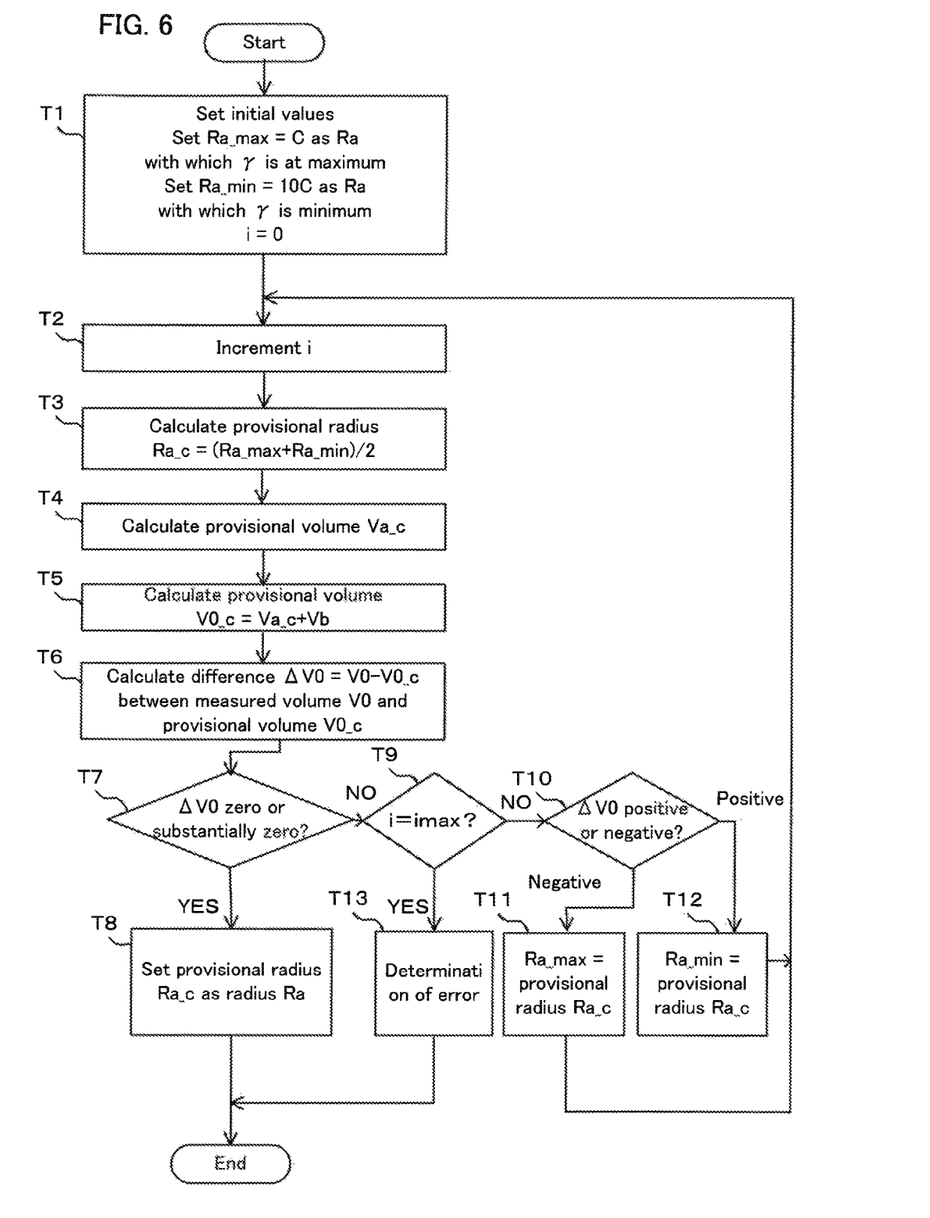
FIG. 6 is a flowchart illustrating a flow of calculation of a curvature radius of an outer surface of the droplet in step S7 of FIG. 5.

FIG. 6 is a flowchart illustrating the flow of calculation of the curvature radius Ra in step S7 of FIG. 5. In processing in step S7, the image processing unit 8 first sets initial values (step T1).

Specifically, the image processing unit 8 sets Ra_max=C ($\alpha$=90°) as the curvature radius Ra with which the contact angle $\gamma$ is theoretically at its maximum. Also, the image processing unit 8 sets Ra_min=10 C ($\alpha$=approximately 5.7°) as the curvature radius Ra with which the contact angle $\gamma$ is virtually at its minimum. Also, the image processing unit 8 sets the initial value of a counter i to zero.

Next, the image processing unit 8 increments the counter i (step T2). That is, the processing "the counter i=i+1" is performed.

Next, the image processing unit 8 sets a provisional radius Ra_c as a provisional curvature radius Ra (step T3). Specifically, the image processing unit 8 calculates the provisional radius Ra_c expressed by the formula below:

$$Ra\_c=(Ra\_max+Ra\_min)/2 \tag{20}$$

That is, the provisional radius Ra_c is the average value of Ra_max and Ra_min.

Next, the image processing unit 8 calculates a provisional volume Va_c as a provisional value of the volume Va of the first region 11 (step T4). The provisional volume Va_c is calculated by setting the volume Va to the provisional volume Va_c and setting the radius Ra to the provisional radius Ra_c in the above-described Formula (12), which is the formula for calculating Va.

Next, the image processing unit 8 calculates a provisional volume V0_c as a provisional value of the volume V0 of the droplet 2 (step T5). The provisional volume V0_c is expressed by the formula below:

$$V0\_c=Va\_c+Vb \tag{21}$$

Next, the image processing unit 8 calculates a difference $\Delta V0$ between the actual volume V0 of the droplet 2 measured from the captured image and the provisional volume V0_c calculated in step T5 (step T6). The difference $\Delta V0$ is expressed by the formula below:

$$\Delta V0=V0-V0\_c \tag{22}$$

Next, the image processing unit 8 determines whether or not $\Delta V0$ is zero or substantially zero (step T7). That is, the image processing unit 8 determines whether or not the provisional volume V0_c calculated based on the provisional radius Ra_c is substantially equal to the actual volume V0 of the droplet 2. That is, the image processing unit 8 determines whether or not the provisional radius Ra_c is substantially equal to the actual radius Ra.

For example, if $-0.0000001<$the difference $\Delta V0<0.0000001$ is satisfied, the image processing unit 8 determines that the difference $\Delta V0$ is zero or substantially zero. On the other hand, if the difference $\Delta V0$ is outside the above-described range, the image processing unit 8 determines that the difference $\Delta V0$ is neither zero nor substantially zero.

If the difference $\Delta V0$ is zero or substantially zero (YES in step T7), the image processing unit 8 sets the provisional radius Ra_c as the radius Ra (step T8). Consequently, the curvature radius Ra is calculated.

On the other hand, if the difference ΔV0 is neither zero nor substantially zero (NO in step T7), the image processing unit 8 determines the value of the counter i (step T9). If the value of the counter i has not reached a predetermined upper limit value imax (for example, imax=50) (NO in step T9), the image processing unit 8 corrects the setting value Ra_max or the setting value Ra_min (steps T10, T11, and T12).

Specifically, if the difference ΔV0 is a negative value (NEGATIVE in step T10), that is, if the provisional volume V0_c is larger than the actual volume V0, the image processing unit 8 sets the value of Ra_max to the value of the provisional radius Ra_c calculated in previous step T3 (step T11). In other words, the image processing unit 8 performs processing to reduce the provisional volume V0_c that is to be calculated in subsequent step T5.

On the other hand, if the difference ΔV0 is a positive value (POSITIVE in step T10), that is, if the provisional volume V0_c is smaller than the actual volume V0, the image processing unit 8 sets the value of Ra_min to the value of the provisional radius Ra_c calculated in previous step T3 (step T12). In other words, the image processing unit 8 performs processing to increase the provisional volume V0_c that is to be calculated in subsequent step T5.

After correcting the value of Ra_max in step T11 or correcting the value of Ra_min in step T12, the image processing unit 8 repeats the processing in step T2 to step T7 again.

In another instance of processing in step T7, if the difference ΔV0 is zero or substantially zero (YES in step T7), the image processing unit 8 sets the provisional radius Ra_c as the radius Ra (step T8).

On the other hand, if the difference ΔV0 is neither zero nor substantially zero in another instance of processing in step T7 as well (NO in step T7), the image processing unit 8 determines the value of the counter i (step T9). If this is the case, the image processing unit 8 repeats the processing in steps T2 to T7, the processing in steps T9 to T10, and the processing in step T11 or step T12 until the value of ΔV0 becomes zero or substantially zero, or until the value of the counter i reaches the predetermined upper limit value imax.

On the other hand, upon determining in step T9 that the value of the counter i has reached imax (YES in step T9), the image processing unit 8 sets an error flag (step T13). That is, the image processing unit 8 determines that the calculation of the provisional radius Ra_c has not converged.

Referring to FIG. 1 and FIG. 2, the value of the contact angle γ calculated by the above-described configuration is output to the inspection unit 4.

The inspection unit 4 includes, for example, a CPU, a RAM, and a ROM. The inspection unit 4 inspects the wettability of the sample curved surface 104 by using the contact angle γ measured by the contact-angle measurement device 3. Specifically, if the contact angle γ is smaller than or equal to a predetermined threshold value, the inspection unit 4 determines that the contact angle γ is sufficiently small and that the wettability of the sample curved surface 104 is at an acceptable level.

On the other hand, if the contact angle γ is larger than the aforementioned threshold value, the inspection unit 4 determines that the contact angle γ is large and that the wettability of the sample curved surface 104 is at an unacceptable level. The inspection unit 4 displays the results of inspection on a display unit, which is not shown in the drawings.

Program

A program according to the bioprosthetic-member inspection device 1 according to the present embodiment suffices if it is a program that causes a computer to execute the processing for the bioprosthetic-member inspection device 1. The bioprosthetic-member inspection device 1, the contact-angle measurement device 3, and the contact-angle measurement method according to the present embodiment can be realized by installing the program to the computer and executing the program. If this is the case, the CPU (Central Processing Unit) of the computer functions as the image processing unit 8 and the inspection unit 4, and performs processing. Note that the bioprosthetic-member inspection device 1 may be realized by cooperation between software and hardware as in the present embodiment, or by hardware.

As described above, with the bioprosthetic-member inspection device 1 according to the present embodiment, the image processing unit 8 corrects the apparent contact angle α by using the inclination angle β of the sample curved surface 104. In other words, the image processing unit 8 calculates the true contact angle γ that takes the shape of the sample curved surface 104 into consideration. Consequently, the bioprosthetic-member inspection device 1 can precisely measure the contact angle γ of the sample curved surface 104.

Also, with the bioprosthetic-member inspection device 1, the apparent contact angle α is an angle formed by the plane P0 that includes the outer periphery portion 2a, and the plane L2 related to the droplet 2. With such a configuration, an angle with reference to the outer periphery portion 2a of the droplet 2 is set as the apparent contact angle α.

Also, with the bioprosthetic-member inspection device 1, the inclination angle β is an angle formed by the plane P0 that includes the outer periphery portion 2a and the plane L1 related to the sample curved surface 104. With such a configuration, an angle with reference to the outer periphery portion 2a of the droplet 2 is set as the inclination angle β.

Also, with the bioprosthetic-member inspection device 1, the image processing unit 8 calculates the curvature radius Ra of the outer surface 2b of the droplet 2 by using the curvature radius C of the outer periphery portion 2a, the volume V0 of the droplet 2, and the curvature radius Rb of the sample curved surface 104 (step S7). The image processing unit 8 then calculates the apparent contact angle α by using the curvature radius Ra and the curvature radius C (step S9). With this configuration, it is relatively difficult to measure the curvature radius Ra of the outer surface 2b of the droplet 2 supplied to the dent 103 of the sample curved surface 104 that is not flat, directly from the captured image. In contrast, it is relatively easy to measure the curvature radius C of the outer periphery portion 2a of the droplet 2 from the captured image (the flat image) obtained by the image capturing unit 7. Also, it is relatively easy to measure the volume V0 of the droplet 2 by measuring the droplet 2 ejected from the nozzle 9 from the captured image. Also, it is relatively easy to obtain the curvature radius Rb of the sample curved surface 104 from the design data of the sample 100 or the like. Therefore, it is easy for the image processing unit 8 to calculate the curvature radius Ra of the outer surface 2b of the droplet 2 by using the curvature radius C of the outer periphery portion 2a, the volume V0 of the droplet 2, and the curvature radius Rb of the sample curved surface 104, as data that can be relatively easily obtained. The image processing unit 8 can calculate the apparent contact angle α by applying the curvature radius Ra of the outer surface 2b and the curvature radius C of the outer periphery portion 2a to trigonometric functions.

Also, with the bioprosthetic-member inspection device 1, the curvature radius Ra of the outer surface 2b is calculated by using Formulas (12), (13), and (14). With this configuration, it is possible to calculate the volume Va of the first region 11 by using Formula (12) for calculating the volume of a portion of the sphere Sa. Also, it is possible to calculate the volume Vb of the second region 12 by using Formula (13) for calculating the volume of a portion of the sphere Sb. It is then possible to calculate the curvature radius Ra by using Formula (14) that expresses the relationship among the volume V0 of the droplet 2, the volume Va of the first region 11, and the volume Vb of the second region 12.

Also, with the bioprosthetic-member inspection device 1, the image processing unit 8 calculates the inclination angle β by using the curvature radius C of the outer periphery portion 2a and the curvature radius Rb of the sample curved surface 104 (step S10). With this configuration, it is relatively easy to measure the curvature radius C of the outer periphery portion 2a of the droplet 2 from the captured image obtained by the image capturing unit 7. Also, it is relatively easy to obtain the curvature radius Rb of the sample curved surface 104 from the design data of the sample 100 or the like. Therefore, the image processing unit 8 can easily calculate the inclination angle β.

Also, with the bioprosthetic-member inspection device 1, the curvature radius C of the outer periphery portion 2a is calculated by using the captured image obtained by the image capturing unit 7. With this configuration, the outer periphery portion 2a can be easily seen from the outside of the droplet 2. Therefore, it is easy to calculate the curvature radius C of the outer periphery portion 2a based on the captured image.

Also, with the bioprosthetic-member inspection device 1, the sample curved surface 104 is a concave curved surface having the predetermined curvature radius Rb, and the image processing unit 8 calculates the value of the apparent contact angle α to which the inclination angle β has been added, as the contact angle γ (step S11). With this configuration, the image processing unit 8 can calculate the true contact angle γ of the sample curved surface 104 having a concave shape. The droplet 2 on the sample curved surface 104 having a concave shape is surrounded by the sample 100, and it is difficult to visually measure the contact angle γ from the side of the sample 100. However, even in such a case, the image processing unit 8 can precisely calculate the true contact angle γ of the sample curved surface 104.

Also, with the bioprosthetic-member inspection device 1, the volume V0 of the droplet 2 is set to 0.5µ liters to 3.0µ liters. By setting the volume V0 of the droplet 2 to be larger than or equal to 0.5µ liters, it is possible to reduce the amount of liquid that remains in the nozzle 9 when the droplet 2 is dripped from the nozzle 9. Consequently, it is possible to sufficiently reduce the proportion of liquid that remains in the nozzle 9 to the volume of the droplet 2 supplied from the nozzle 9. Therefore, it is possible to sufficiently reduce the influence of the liquid remaining in the nozzle 9 with respect to the droplet 2 on the sample curved surface 104, and it is possible to more precisely calculate the contact angle γ by using the droplet 2. Also, by setting the volume V0 of the droplet 2 to be smaller than or equal to 3.0µ liters, it is possible to prevent the volume V0 of the droplet 2 that has dropped to the sample curved surface 104 from becoming too large. Therefore, it is possible to reduce the influence of gravity on the droplet 2 on the sample curved surface 104. Consequently, it is possible to treat the outer surface 2b of the droplet 2 as a portion of a virtually true sphere, and more precisely calculate the contact angle γ by using the droplet 2.

Modifications

Although an embodiment of the present invention has been described, the present invention is not limited to the above-described embodiment, and may be modified in various manners within the scope of CLAMS. For example, the present invention may be implemented with the following modifications.

(1) In the above-described embodiment, the image processing unit 8 calculates the apparent contact angle α by using the curvature radius Ra of the outer surface 2b of the droplet 2 and the curvature radius C of the outer periphery portion 2a, and calculates the inclination angle β by using the curvature radius Rb of the sample curved surface 104 and the curvature radius C. However, the present invention is not limited in this way. The image processing unit 8 may calculate the apparent contact angle α and the inclination angle β by using the θ/2 method, for example.

Specifically, referring to FIG. 2, an angle α' formed by a plane L3 and the plane P0 is ½ of the apparent contact angle α, i.e., α'=α/2 is satisfied, where the plane L3 is a plane rotated from the plane P0 about a tangent line to the outer periphery portion 2a at a given point on the outer periphery portion 2a so as to be located passing through the top point 2c. Therefore, the apparent contact angle α can be obtained by multiplying the angle α' by two.

Also, an angle β' formed by a plane L4 and the plane P0 is ½ of the inclination angle β, i.e., β'=β/2 is satisfied, where the plane L4 is a plane rotated from the plane P0 about a tangent line to the outer periphery portion 2a at a given point on the outer periphery portion 2a so as to be located passing through a center point 2d of the bottom surface of the droplet 2. Therefore, the inclination angle β can be obtained by multiplying the angle β' by two.

Figure 7:
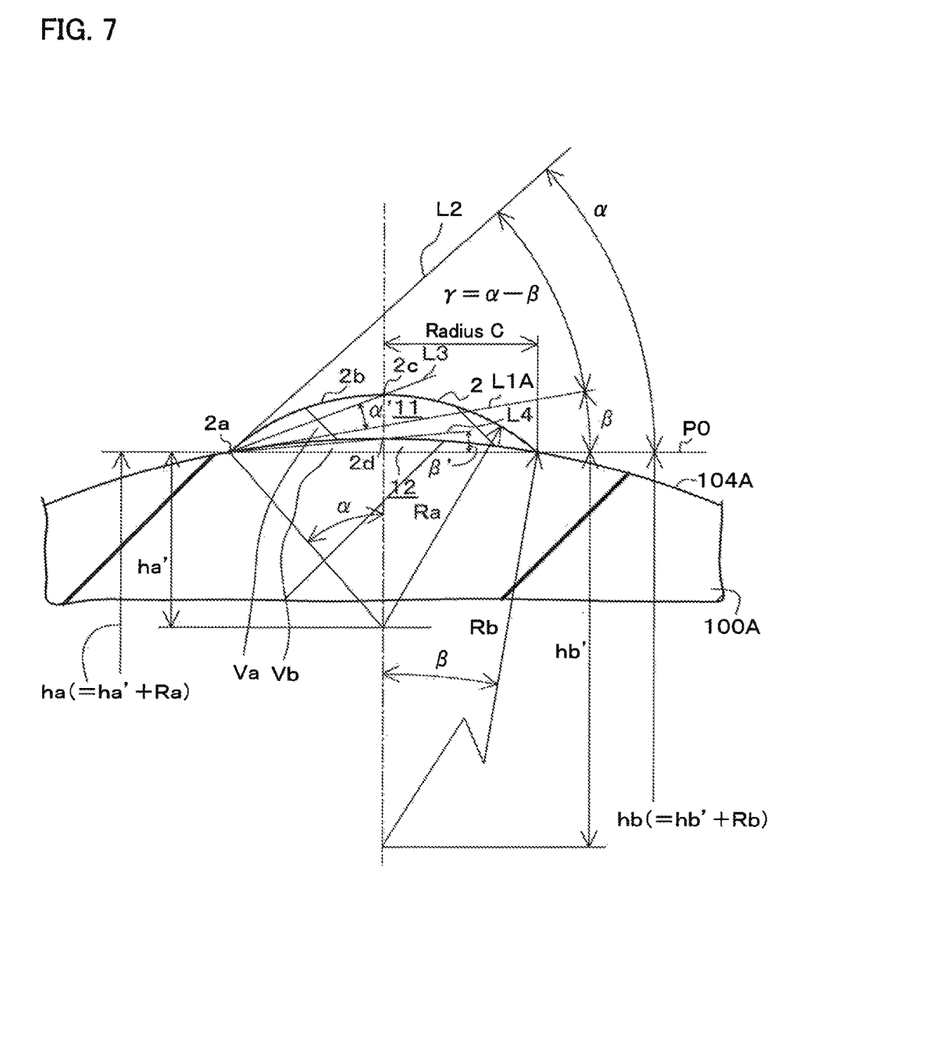
FIG. 7 is a cross-sectional view according to a modification of the present invention, in which a sample and a droplet are enlarged.

(2) In the above-described embodiment, a description is given of an exemplary mode in which the sample curved surface 104 is a concave curved surface. However, the present invention is not limited in this way. For example, as shown in FIG. 7, the contact angle γ of a sample curved surface 104A having a convex shape may be calculated.

Note that the following mainly describes the differences from the configuration of the above-described embodiment, and the like constituent elements as those of the above-described embodiment are given the same reference numerals and the description thereof is omitted.

In this case, a sample 100A is, for example, a bone head ball for an artificial hip joint. The sample 100A is a spherical member that is fixed to the tip of a stem (not shown in the drawings) that is embedded in a distal portion of the femur of the patient. The sample 100A is configured so as to be brought into sliding-contact with the sample curved surface 104 of the above-described sample 100 (liner). A sample curved surface 104A of the sample 100A is configured with the like coating layer as that of the sample curved surface 104.

The sample curved surface 104A is formed to have a spherical shape with the predetermined curvature radius Rb. In this modification, the sample curved surface 104A is a convex curved surface having the predetermined curvature radius Rb. The outer surface 2b of the droplet 2 has the predetermined curvature radius Ra. The curvature radius of the outer periphery portion 2a is the curvature radius C.

The contact angle γ is the angle formed by a plane L1A related to the sample curved surface 104A and the plane L2 related to the droplet 2. The plane L1A is a plane that includes a tangent line to the sample curved surface 104A at a given point on the outer periphery portion 2a, and that is in contact with the sample curved surface 104A. The plane L1A includes a plurality of tangent lines to the sample curved surface 104A at a given point on the outer periphery portion 2a. The plane L2 is a plane that includes a tangent line to an outer surface 2b of the droplet 2 at a given point on the outer periphery portion 2a, and that is in contact with the outer surface 2b. The plane L2 includes a plurality of tangent lines to the outer surface 2b at a given point on the outer periphery portion 2a.

The image processing unit 8 is configured to calculate the contact angle γ based on, for example, the image data obtained by capturing an image of the droplet 2 and the sample curved surface 104A.

Next, a description is given of, for example, principles (calculation expressions) for calculating the contact angle γ of the sample curved surface 104A by using the image processing unit 8.

For the calculation of the contact angle γ, first, the volumes Va and Vb related to the droplet 2 and the sample 100A are calculated. The volume Va is the volume of the first region 11 that is the region surrounded by the plane P0 (a horizontal plane in the present modification) that includes the outer periphery portion 2a, and the outer surface 2b of the droplet 2 (the surface of an exposed portion of the droplet 2 above the sample curved surface 104A). The volume Vb is the volume of the second region 12 that is the region surrounded by the plane P0 and the sample curved surface 104A.

The formula for calculating the volume Va of the first region 11 and the formula for calculating the volume Vb of the second region 12 are the same as the above-described Formula (12) and Formula (13), respectively. In this case, the value of the volume Va of the first region 11 from which the volume Vb of the second region 12 has been subtracted is the volume V0 of the droplet 2, which is expressed by V0=Va−Vb (23). Formula (23) is an example of "Formula (c)" according to the present invention.

Here, the image processing unit 8 can measure the curvature radius C of the outer periphery portion 2a from the captured image (the flat image) obtained by the image capturing unit 7. The image processing unit 8 can obtain the curvature radius Rb of the sample curved surface 104A from, for example, the design data of the sample 100A. The image processing unit 8 can also measure the volume V0 of the droplet 2 from the data of the captured image of the droplet 2 immediately before it drops from the nozzle 9. That is, using the curvature radius C, the curvature radius Rb, and the volume V0 of the droplet 2 as known values, the image processing unit 8 can calculate the curvature radius Ra of the first region 11 by using Formulas (12), (13), and (23).

The angle formed by the plane L2 related to the droplet 2 and the plane P0 that includes the outer periphery portion 2a (the angle that faces toward the top point 2c) is the contact angle with respect to the first region 11, and this angle is defined as the apparent contact angle α of the droplet 2.

In side view, the angle formed by the plane L1A related to the sample curved surface 104A, and the plane P0, is the contact angle with respect to the second region 12, and this angle is defined as the inclination angle β of the sample curved surface 104A.

The relationships expressed by the above-described formulas (15) and (16) are satisfied with the apparent contact angle α and the inclination angle β.

That is, the above-described Formula (17) for the apparent contact angle α is satisfied, and the above-described Formula (18) for the inclination angle β is satisfied, in this modification as well. In the present modification, as can be seen from FIG. 7, the contact angle γ=α−β . . . (24) is satisfied.

Note that the flow of calculation of the contact angle γ of the sample 100A by the contact-angle measurement device 3 is the same as the flow shown in FIG. 5 and FIG. 6 (steps S1 to S13 and T1 to T13) except that V0=Va−Vb (V0_c=Va_c−Vb) is satisfied and the contact angle γ (=α−β) is calculated by subtracting the inclination angle β from the apparent contact angle α. Therefore, a description of the details of the flow of calculation of the contact angle γ related to the sample 100A is omitted.

As described above, according to this modification, the sample curved surface 104A is a convex curved surface having the predetermined curvature radius Rb, and the image processing unit 8 calculates the value of the apparent contact angle α from which the inclination angle β has been subtracted, as the contact angle γ (α−β). With this configuration, it is possible to calculate the true contact angle γ of the sample curved surface 104A having a convex shape.

Note that when measuring the contact angle γ of the sample curved surface 104A, the image processing unit 8 may calculate the apparent contact angle α and the inclination angle β by using the θ/2 method, for example.

Specifically, referring to FIG. 7, the angle α' formed by the plane L3 and the plane P0 is ½ of the apparent contact angle α, i.e., α'=α/2 is satisfied, where the plane L3 is a plane rotated from the plane P0 about a tangent line to the outer periphery portion 2a at a given point on the outer periphery portion 2a so as to be located passing through the top point 2c. Therefore, the apparent contact angle α can be obtained by multiplying the angle α' by two.

Also, the angle β' formed by the plane L4 and the plane P0 is ½ of the inclination angle β, i.e., β'=β/2 is satisfied, where the plane L4 is a plane rotated from the plane P0 about a tangent line to the outer periphery portion 2a at a given point on the outer periphery portion 2a so as to be located passing through the center point 2d of the bottom surface of the droplet 2. Therefore, the inclination angle β can be obtained by multiplying the angle β' by two.

(3) Note that in the above-described embodiment and modification, a description is given of contact-angle measurement for a liner and a bone head ball for an artificial hip joint as bioprosthetic members. However, the present invention is not limited in this way. A femur implant and a tibia implant for an artificial knee joint may be inspected as bioprosthetic members. Also, the contact angle regarding members other than bioprosthetic members may be inspected by using the contact-angle measurement device according to the present invention.

INDUSTRIAL APPLICABILITY

The present invention is broadly applicable as a contact-angle measurement method, a contact-angle measurement device, a bioprosthetic-member inspection device, and a storage medium.

DESCRIPTIONS OF REFERENCE NUMERALS

1 Bioprosthetic-member inspection device
2 Droplet
2a Outer periphery portion
2b Outer surface of droplet
3 Contact-angle measurement device
4 Inspection unit 8 Image processing unit (apparent contact-angle calculation unit, inclination angle calculation unit, contact-angle calculation unit)
104, 104A Sample curved surface
500 Storage medium
C Curvature radius of outer periphery portion
L1, L1A Plane in contact with sample curved surface
L2 Plane in contact with outer surface of droplet
P0 Plane including outer periphery portion
Ra Curvature radius of outer surface of droplet
Rb Curvature radius of sample curved surface
V0 Volume of droplet
Va Volume of first region surrounded by plane including outer periphery portion and by outer surface of droplet.
Vb Volume of second region surrounded by plane including outer periphery portion and by sample curved surface.
α Apparent contact angle
β Inclination angle
γ Contact angle

The invention claimed is:

1. A contact-angle measurement method for measuring hydrophilic properties of a bioprosthetic, the method comprising:
dripping a droplet on to a curved surface of the bioprosthetic, wherein the curved surface of the bioprosthetic is a concave curved surface having a curvature radius Rb;
capturing an image of the droplet on the curved surface of the bioprosthetic;
calculating an apparent contact-angle α of the droplet and the curved surface of the bioprosthetic based on the image;
calculating an inclination angle β of the curved surface of the bioprosthetic at an outer periphery portion of a contact portion between the droplet and the curved surface of the bioprosthetic based on the image;
calculating a contact angle γ by adding the apparent contact angle α to the inclination angle β of the curved surface of the bioprosthetic; and
determining the hydrophilic properties of the bioprosthetic based on the contact angle γ.

2. The method according to claim 1,
wherein the apparent contact angle α is an angle formed by: a plane that includes a tangent line to an outer surface of the droplet at a given point on the outer periphery portion, and that is in contact with the outer surface; and a plane that includes the outer periphery portion.

3. The method according to claim 1,
wherein the inclination angle β is an angle formed by: a plane that includes a tangent line to the curved surface of the bioprosthetic at a given point on the outer periphery portion, and that is in contact with the curved surface of the bioprosthetic; and a plane that includes the outer periphery portion.

4. The method according to claim 1, further comprising:
calculating a curvature radius Ra of an outer surface of the droplet by using a curvature radius C of the outer periphery portion, a volume V0 of the droplet, and the curvature radius Rb of the curved surface of the bioprosthetic, prior to the calculating the apparent contact-angle,
wherein, in the calculating the apparent contact-angle, the apparent contact angle α is calculated by using the curvature radius Ra and the curvature radius C.

5. The method according to claim 4,
wherein the curvature radius Ra of the outer surface is calculated by using Formulas (a), (b), and (c):

$$Va = (4\pi/3)Ra^3 - (\pi/3)\{(Ra^2-C^2)^{(1/2)}+Ra\}^2\{3Ra-(Ra^2-C^2)^{(1/2)}-Ra\}; \quad (a)$$

$$Vb = (4\pi/3)Rb^3 - (\pi/3)\{(Rb^2-C^2)^{(1/2)}+Rb\}^2\{3Rb-(Rb^2-C^2)^{(1/2)}-Rb\}; \text{ and} \quad (b)$$

$$V0 = Va+Vb \text{ (when the curved surface of the bioprosthetic is concave) or } V0=Va-Vb \text{ (when the curved surface of the bioprosthetic is convex)}, \quad (c)$$

where Va denotes a volume of a first region that is surrounded by: a plane that includes the outer periphery portion; and the outer surface of the droplet, and Vb denotes a volume of a second region that is surrounded by: the plane that includes the outer periphery portion; and the curved surface of the bioprosthetic.

6. The method according to claim 1,
wherein in the calculating the inclination angle, the inclination angle β is calculated by using a curvature radius C of the outer periphery portion and the curvature radius Rb of the curved surface of the bioprosthetic.

7. The method according to claim 4,
wherein the curvature radius C of the outer periphery portion is calculated based on the image.

8. The method according to claim 1,
wherein a volume V0 of the droplet is set to 0.5μ liters to 3.0μ liters.

9. A measurement device for measuring hydrophilic properties of a bioprosthetic, the measurement device comprising:
a camera;
a drip unit that releases a droplet of a predetermined size;
a memory; and
a processor communicatively coupled to the camera, the drip unit and the memory,
wherein the processor:
causes the drip unit to release the droplet,
captures, using the camera, an image of the droplet on a curved surface of the
bioprosthetic, wherein the curved surface of the bioprosthetic is a concave curved surface having a curvature radius Rb,
calculates an apparent contact-angle α of the droplet and the curved surface of the bioprosthetic based on the image;
calculates an inclination angle β of the curved surface of the bioprosthetic at an outer periphery portion of a contact portion of the droplet and the curved surface of the bioprosthetic based on the image,
calculates the contact angle γ by adding the apparent contact angle α using the inclination angle β, and
determines the hydrophilic properties of the bioprosthetic based on the contact angle γ.

10. The measurement device according to claim 9,
wherein the hydrophilic properties include a wettability of the curved surface of the bioprosthetic.

11. A contact-angle measurement method for measuring hydrophilic properties of a bioprosthetic, the method comprising:
dripping a droplet on to a curved surface of the bioprosthetic, wherein the curved surface of the bioprosthetic is a convex curved surface having a curvature radius Rb;
capturing an image of the droplet on the curved surface of the bioprosthetic;

calculating an apparent contact-angle α of the droplet and the curved surface of the bioprosthetic based on the image;

calculating an inclination angle β of the curved surface of the bioprosthetic at an outer periphery portion of a contact portion between the droplet and the curved surface of the bioprosthetic based on the image;

calculating a contact angle γ by subtracting the inclination angle β of the curved surface of the bioprosthetic from the apparent contact angle α; and determining the hydrophilic properties of the bioprosthetic based on the contact angle γ.

12. A measurement device for measuring hydrophilic properties of a bioprosthetic, the measurement device comprising:

a camera;

a drip unit that releases a droplet of a predetermined size;

a memory; and a processor communicatively coupled to the camera, the drip unit and the memory, wherein the processor:

causes the drip unit to release the droplet, captures, using the camera, an image of the droplet on a curved surface of the bioprosthetic, wherein the curved surface of the bioprosthetic is a convex curved surface having a curvature radius Rb, calculates an apparent contact-angle α of the droplet and the curved surface of the bioprosthetic based on the image;

calculates an inclination angle β of the curved surface of the bioprosthetic at an outer periphery portion of a contact portion of the droplet and the curved surface of the bioprosthetic based on the image, calculates the contact angle γ by subtracting the inclination angle β from the apparent contact angle α, and determines the hydrophilic properties of the bioprosthetic based on the contact angle γ.

13. The method according to claim 11, wherein the apparent contact angle α is an angle formed by: a plane that includes a tangent line to an outer surface of the droplet at a given point on the outer periphery portion, and that is in contact with the outer surface; and a plane that includes the outer periphery portion.

14. The method according to claim 11, wherein the inclination angle β is an angle formed by: a plane that includes a tangent line to the curved surface of the bioprosthetic at a given point on the outer periphery portion, and that is in contact with the curved surface of the bioprosthetic; and a plane that includes the outer periphery portion.

15. The method according to claim 11, further comprising:

calculating a curvature radius Ra of an outer surface of the droplet by using a curvature radius C of the outer periphery portion, a volume V0 of the droplet, and the curvature radius Rb of the curved surface of the bioprosthetic, prior to the calculating the apparent contact-angle, wherein, in the calculating the apparent contact-angle, the apparent contact angle α is calculated by using the curvature radius Ra and the curvature radius C.

16. The method according to claim 15, wherein the curvature radius Ra of the outer surface is calculated by using Formulas (a), (b), and (c):

$$Va = (4\pi/3)Ra^3 - (\pi/3)\{(Ra^2 - C^2)^{(1/2)} + Ra\}^2\{3Ra - (Ra^2 - C^2)^{(1/2)} - Ra\}; \quad (a)$$

$$Vb = (4\pi/3)Rb^3 - (\pi/3)\{(Rb^2 - C^2)^{(1/2)} + Rb\}^2\{3Rb - (Rb^2 - C^2)^{(1/2)} - Rb\}; \text{ and} \quad (b)$$

$$V0 = Va + Vb \text{ (when the curved surface of the bioprosthetic is concave) or } V0 = Va - Vb \text{ (when the curved surface of the bioprosthetic is convex)}, \quad (c)$$

where Va denotes a volume of a first region that is surrounded by: a plane that includes the outer periphery portion; and the outer surface of the droplet, and Vb denotes a volume of a second region that is surrounded by: the plane that includes the outer periphery portion; and the curved surface of the bioprosthetic.

17. The method according to claim 11, wherein in the calculating the inclination angle, the inclination angle β is calculated by using a curvature radius C of the outer periphery portion and the curvature radius Rb of the curved surface of the bioprosthetic.

18. The method according to claim 15, wherein the curvature radius C of the outer periphery portion is calculated based on the image.

19. The method according to claim 11, wherein a volume V0 of the droplet is set to 0.5µ liters to 3.0µ liters.

* * * * *